US005674694A

United States Patent [19]
Ross

[11] Patent Number: 5,674,694
[45] Date of Patent: Oct. 7, 1997

[54] CLONOGENIC ASSAY FOR DETECTING MICRO LEVELS OF TUMOR CELLS IN HEMATOPOIETIC SAMPLES

[75] Inventor: Amelia Ann Ross, Los Angeles, Calif.

[73] Assignee: Biologic & Immunologic Science Laboratories, Inc., Reseda, Calif.

[21] Appl. No.: 319,410

[22] Filed: Oct. 6, 1994

Related U.S. Application Data

[63] Continuation-in-part of Ser. No. 124,986, Sep. 21, 1993, abandoned.

[51] Int. Cl.$^6$ .................... G01N 33/574; G01N 33/48; C12Q 1/04; C12N 5/00
[52] U.S. Cl. .................... 435/7.23; 435/34; 435/347; 435/366; 435/373; 436/64
[58] Field of Search .................... 435/7.23, 240.1, 435/240.2, 240.21; 424/9.1; 436/64

[56] References Cited

U.S. PATENT DOCUMENTS

| | | | |
|---|---|---|---|
| 4,411,990 | 10/1983 | Salmon et al. | 435/32 |
| 4,844,893 | 7/1989 | Honsik et al. | 424/85.2 |
| 5,081,030 | 1/1992 | Civin | 435/240.2 |
| 5,192,553 | 3/1993 | Boyse | 424/529 |

OTHER PUBLICATIONS

Aapro et al., *Eur. J. Cancer* 27(3):231–235 (1991).
Berger et al., *A.J.C.P.* 90(1):1–6 (1988).
Borinaga et al., *Brit. J. Haematology* 76:476–483 (1990).
Brugger et al., *Blood* 81(10):2579–2584 (1993).
Caracciolo et al., *Brit. J. of Haematology* 72:306–311 (1989).
Cashman et al., *Leukemia* 6(9):886–892 (1992).
Cote et al., *J. Clinical Oncology* 9(10):1749–1756 (1991).
Diel et al., *J. Clinical Oncology* 10(10):1534–1539 (1992).
Frappaz et al., *Neurosurgery* 23(3):355–359 (1988).
Freedman et al., *Blood* 81(11):3068–3075 (1993).
Gadazar et al., *J. Natl. Can. Inst.* 82(2):117–124 (1990).
Hamburger et al., *Science* 197:461–463 (1977).
Hoang et al., *J. Exp. Med.* 168:463–474 (1988).
Hogge et al., *Blood* 77(3):493–499 (1991).
Jansen et al., *Leukemia* 7(4) 643–645 (1993).
Joshi et al., *Bone Marrow Transplantation* 6:179–183 (1990).
Manni et al., *Breast Can. Res. & Treat.* 20:43–52 (1991).
Metcalf et al., *Proc. Natl. Acad. Sci. USA* 89:2819–2823 (1992).
Moore et al., *Blood* 79(6):1393–1399 (1992).
Ode et al., *Leukemia* 6(11):1210–1212 (1992).
Pathak et al., *Int. J. Cancer* 30:745–750 (1982).
Ponting et al., *Growth Factors* 4:165–173 (1991).
Von Hoff, *Can. & Metastasis Rev.* 7:357–371 (1988).
Vredenburgh et al., *Breast Cancer Res. Treat.* 19:171 (1991).
Ross et al., *Amer. J. Clin. Pathology* 98(3):347 (1992).
Ross et al., *Proceedings of ASCO* 12:69 (1993).
Ross et al., *Blood* 80:235a (1992).
Ross et al., *Cancer Res. Treat.* 23:166 (1992).
Ross et al., *Blood* 78(1):248a (1991).
Ross et al., *Breast Cancer Res. Treat.* 19:161 (1991).
Salmon et al., *New England J. of Med.* 298(24):1321–1327 (1978).
Sharp et al., *Blood* 79(4):1074–1080 (1992).
Cote, et al., *Am. J. Surg. Pathol.* 12:333 (1988).
Mansi, et al., *J. Clin. Oncol.* 7:445 (1989).
Redding, et al., *Lancet* 2:1271 (1983).
Ali–Osman, et al. *Cancer Research* 48:715–724, 1988.
Cote, R.J. et al. American Journal of Surgical Pathology 12(5):333–340, 1988.
Hanauske, A.R. et al. Cancer 61:1832–1837, 1988.
Moss, T.J. et al. Proceedings of the Annual Meeting of the American Society of Clinical Oncology. 12:321 (Abst.#1064), 1993.
Nachbaur, D. et al. Cancer Letters 50:197–201, 1990.
Ross, A.R. et al. Blood, 82(9):2605–2610, 1990.

*Primary Examiner*—Lila Feisee
*Assistant Examiner*—Yvonne Eyler
*Attorney, Agent, or Firm*—Townsend and Townsend and Crew LLP

[57] ABSTRACT

The present invention relates to a clonogenic assay that is effective for detecting micro levels of tumor cells in patient hematopoietic samples, methods for aiding in determining the prognosis of a patient having such tumor cells, and methods for determining which drugs will be effective or will not be effective against a particular patient's tumor cells.

17 Claims, No Drawings

CLONOGENIC ASSAY FOR DETECTING MICRO LEVELS OF TUMOR CELLS IN HEMATOPOIETIC SAMPLES

This application is a continuation-in-part application of U.S. Ser. No. 08/124,986, filed Sep. 21, 1993, now abandoned, which is incorporated by reference herein.

This invention was made in part with federal government support under Grant No. 1R43 CA57158-01 from the National Institutes of Health and the government may have certain rights in this invention.

FIELD OF THE INVENTION

The present invention relates to a clonogenic assay that is effective for detecting micro levels of tumor cells in patient hematopoietic samples, methods for aiding in determining the prognosis of a patient having such tumor cells, and methods for determining the sensitivity or resistance of such tumor cells to test drugs.

BACKGROUND OF THE INVENTION

The bone marrow is a site of metastases in many cancers. Involvement is particularly common in breast cancer, prostate cancer, small cell lung cancer and malignant lymphomas. The early detection of metastases or primary tumor cells which exist in minute levels in hematopoietic samples is critical to maximizing the benefit of treatment to the cancer patient. The correlation of early detection and treatment with increased survival rates is well known. Further, if the nature of the tumor cell is identified, treatment can be better tailored to the patient's needs.

The bone marrow (BM) appears to be a reservoir for low numbers of tumor cells in patients with no clinically apparent metastatic disease (Redding, et al., *Lancet* 2: 1271 (1983); Cote, et al., *Am. J. Surg. Pathol.* 12: 333 (1988)). However, these cells may be merely dead or dormant cells that have been shed from the primary tumor and, therefore, cannot set up secondary sites of disease. Additionally, some researchers have reported that the tumor micrometastases disappear from the bone marrow following tumor-removing surgery (Mansi, et al., *J. Clin. Oncol.* 7: 445 (1989)). It is generally accepted that breast cancer patients with BM micrometastases have a worse prognosis than those who are micrometastases-free (Cote, et al., *J. Clin. Oncol.* 9: 1749 (1991); Diel, et al., *J. Clin. Oncol.* 10: 1534 (1992)). It is not known if all cells in the bone marrow micrometastases have the capacity to establish secondary sites of disease, or if the patient's prognosis is related to the numbers of micrometastatic tumor cells. Assays which detect viable tumor cells would likely generate a more reliable indicator of prognosis.

Current techniques to detect occult metastases and other micro levels of tumor cells in hematopoietic patient samples, such as from the bone marrow can be tedious, variable or unreliable. Immunohistochemical detection methods are typically used, but they do not provide as accurate an assessment of the patient's condition as is needed since they do not distinguish between viable and nonviable tumor cells.

Tumor culture techniques employing liquid culture rely upon the expansion of tumor cell growth coupled with the death of normal hematopoietic cells over time, which requires an incubation culture period of at least four to six weeks. Further, such techniques are not used to obtain clonogenic growth and present difficulties which are hard to overcome if immunocytochemical tests are to be employed.

Traditionally, human tumor clonogenic assays (HTCA) have been used to test individual tumor specimens in vitro against chemotherapeutic drugs (Hamburger, et al., *Science* 197: 461 (1977); Von Hoff D. D., *Cancer Met. Rev.* 7: 357 (1988)). This type of testing is useful for determining the most effective drug(s) for treating a patient's specific tumor, and assists in eliminating unnecessary toxicity that often results from treatment with ineffective agents. However, the use of HTCA's has been hindered in the clinical setting due to, inter alia, (1) the substantial number of tumor cells required to perform the in vitro testing, and (2) the fact that drug sensitivity of primary tumors may not reflect drug sensitivities of metastatic tumors.

There is thus, a strong need for a sensitive, reliable and rapid assay which permits the detection and growth of viable tumor cells found at micro levels in hematopoietic samples.

SUMMARY OF THE INVENTION

The clonogenic assays described here are highly advantageous because they enable the detection of viable micro levels of tumor cells, they are less labor intensive and more reliable than prior methods and they yield high plating efficiencies of the cells to be detected. Further, since the assay is one which permits the growth of the target tumor cells, the assay yields clones which may be used to assay for drug sensitivity of the tumor cell line.

The clonogenic assays disclosed are particularly suited for obtaining the isolation and clonogenic growth of occult metastatic tumor cells from the bone marrow of cancer patients. This provides at least the following advantages (1) testing of chemotherapeutic drugs can be performed at diagnosis and during therapy because low numbers of metastatic tumor cells present in the marrow can be grown with reasonable efficiency, (2) testing can be done with improved sensitivity and specificity because drug responsiveness of these cells may be more reflective of other systemically established tumor cells, (3) testing can be performed serially to identify emerging drug resistance as treatment proceeds.

The invention includes a clonogenic tumor cell assay for detecting viable micro levels of tumor cells resident in a patient hematopoietic sample that involves the following steps:

(a) obtaining a hematopoietic cell sample containing micro levels of tumor cells;

(b) plating tumor cells and hematopoietic cells from the sample on homogeneous culture media which supports growth of normal hematopoietic cells comprising (i) a gelling agent; and (ii) at least one growth factor which stimulates the growth of the tumor cells; wherein the cell sample is plated at a concentration to yield both individual viable normal cell and tumor cell clones;

(c) incubating the cell sample plate to obtain growth of the clones; then, (d) detecting the presence of micro tumor cell clones.

Preferred growth factors include GM-CSF, EGF, IGF-1, TGF-α, PDGF, Nerve Growth Factor, IL-3 and IL-6. The assay also is uniquely suited to accommodate a detection step wherein the tumor cells are detected by cooling the cell sample clones on the culture media, placing the clones and the culture media on a slide, incubating the clones with a binding moiety specific for a tumor cell marker to create a binding moiety-tumor cell complex and then detecting the presence of the complex, by observation through a fluorescent microscope or other means. The clones may be further incubated with a second binding moiety specific for a second cell marker to create a second binding moiety cell complex which can also be detected. Also, the tumor cell concentration in the hematopoietic sample may advantageously be enriched prior to plating the sample.

The invention also includes a tissue culture plate containing tissue culture media for growing hematopoietic cells, a gelling agent at a concentration of about 0.15 to about 0.6%, normal hematopoietic cells and clones of micro tumor cells selected from the group consisting of breast tumor cells, ovarian tumor cells, prostate tumor cells, colon tumor cells, melanoma cells, neuroblastoma cells, large cell lung tumor cells and small cell lung tumor cells, said clones being separate and isolated from each other such that the number and presence of the micrometastatic clones can be detected by immunocytochemical means.

The assays of the invention can be applied to an in vitro method for measuring drug sensitivity of a tumor cell as an indication of the antineoplastic activity of a drug against a tumor cell, by individually subjecting a test aliquot and a control aliquot of a patient hematopoietic specimen containing suspected micro levels of tumor cells and normal hematopoietic cells to an assay procedure for quantitatively determining the viable colony-forming tumor cell contents thereof, the test aliquot differing from the control aliquot in having been subjected to exposure with the drug to be tested, whereby the drug sensitivity at the drug exposure dose level tested may be determined as the percent reduction in the assay count resulting from the drug exposure, the assay procedure employing the following:

(a) plating the test and the control aliquots on homogenous culture media which supports growth of normal hematopoietic cells comprising (i) a gelling agent; (ii) at least one growth factor which stimulates the growth of the tumor cells; wherein the aliquots are plated separately at a concentration to yield individual viable normal hematopoietic and tumor cell clones; and (b) incubating the cells to obtain growth of the clones; then, (c) determining the number of tumor cell clones in the test and control aliquot plates. The test aliquot may be subjected to the drug prior to mixing the test aliquot with the culture media or the test aliquot is subjected to the drug when plated in the culture media which contains the drug.

The invention also includes a method for determining the effectiveness of a bone marrow treatment technique comprising, testing a specimen of bone marrow cells prior to a treatment (pre-treatment cells) and a specimen of the bone marrow cells after a treatment (post-treatment cells) for cells of interest by:

(a) plating each specimen on homogenous culture media which supports growth of bone marrow cells comprising (i) a gelling agent; (ii) at least one growth factor which stimulates the growth of cells of interest; wherein the cells are plated at a concentration to yield individual viable clones of bone marrow cells; and (b) incubating the cells to obtain growth of the clones; then, (c) detecting the presence and number of individual clones of cells of interest, resulting from the culturing of each specimen; then, (d) determining whether the post-treatment cells resulted in a decrease or an increase in the number of clones of cells of interest from the pre-treatment cells.

The invention further includes a method of determining the extent that a patient has viable metastatic tumor cells comprising:

(a) plating a patient bone marrow specimen containing suspected micrometastatic tumor cells and bone marrow cells on homogenous culture media which supports growth of bone marrow cells comprising (i) a gelling agent; (ii) at least one growth factor which stimulates the growth of the tumor cells; wherein the cells are plated at a concentration to yield individual viable bone marrow and tumor cell clones; and (b) incubating the cells to obtain growth of the clones; then, (c) detecting the number of individual clones of micrometastatic tumor cells as an indication of the extent of viable micrometastic tumor cells present in the patient.

The invention also includes a clonogenic tumor cell assay for detecting tumor cells resident in a patient sample containing tumor cells comprising:

(a) plating a patient sample on culture media in a culture dish which supports growth of the tumor cells and contains a gelling agent;

(b) incubating the cells to obtain growth of tumor cell clones; then (c) detecting the number and identity of the tumor cell clones by cooling the culture media with the clones (CMC) to release the CMC from its culture dish and placing the CMC on a microscope slide, incubating the CMC with a binding moiety specific for the tumor cells, and then detecting the binding moiety bound to the tumor cells as an indication of the number and identity of the tumor cell clones.

DETAILED DESCRIPTION

The clonogenic assays of the present invention are uniquely designed to permit the detection and quantification of viable micro levels of tumor cells found in patient hematopoietic samples such as bone marrow (BM) specimens or in peripheral blood stem cell (PBSC) specimens. These assays permit the growth of the tumor cells in a system that mimics the environment in which the tumor cell is found. The specimens are plated on semi-solid media which is conducive to both the growth of normal hematopoietic cells and the tumor cells. Since the assays are very efficient, accurate and determine only viable tumor cells they have many applications.

Besides determining the presence or number of such cells, the assays may be used to determine whether the micro level tumor cells are sensitive to known or to new drugs, to determine the efficacy of techniques to manipulate hematopoietic products, such as bone marrow purging techniques, and to assist in determining a patient's prognosis.

The following definitions are provided to facilitate the description of the invention:

"Clone" refers to a colony of cells derived from a single cell.

"Micro levels of tumor cells" in a hematopoietic sample refer to hematopoietic samples which have tumor cells at a level of 500 tumor cells or less per 100,000 normal hematopoietic cells or tumor cells which are otherwise present in such minute quantities that they are not detected by standard histological examination. Micro levels of tumor cells in a hematopoietic sample includes micrometastatic or occult metastatic tumor cells which are readily detected in bone marrow samples or PBSC samples by the methods described here. Those skilled in the art can identify tumor cells immunohistologically and distinguish them from normal hematopoietic cells, which for the purposes of this invention are those non-tumor cells resident in the hematopoietic sample.

Clonogenic Assay for Detection of Micro Levels of Tumor Cells in a Hematopoietic Sample.

In the assays of this invention, hematopoietic samples are collected from patients suspected of having micro levels of tumor cells. Bone marrow specimens or peripheral blood stem cell specimens are of particular interest and are typically collected in situations where micro levels of tumors are suspected in the bone marrow. They are collected by means known in the art. Typically, bone marrow aspirates are obtained through either puncture aspiration from convenient locations, particularly the posterior iliac crest, or from bone marrow harvest. Peripheral blood stem cell samples can be obtained by a venous puncture or leukapheresis procedure. In the case of PBSC samples, patients typically are given chemotherapy or hematopoietic growth factors to enhance the mobilization of stem cells into the peripheral blood. Micro levels of tumor cells obtained from pleural or peritoneal aspirations as well as cerebral spinal fluid can also be used. The specimens should be collected aseptically and stored at room temperature or preserved by cryopreservation in sterile culture media.

The specimens to be assayed are processed by methods known and available in the art with the objective of maintaining the viability of the cells. See, for example, Moss et al., *Blood* 76:1879 (1990). Cryopreserved specimens should be thawed rapidly, by, for example, in a 37° C. water bath. The specimens should be washed in common reagents such as culture media and fetal bovine serum to remove autologous serum proteins and to provide a nutrient source for the cells.

Once the specimens are prepared for plating they are mixed into culture media specifically designed for the micro level tumor cell type suspected to be in the specimen. The samples should be placed directly into the culture media that has been cooled, preferably to about 37° C., at a cell concentration that will yield viable individual clones of normal hematopoietic cells and tumor cells. Such concentration can depend upon the preparation and storage of the specimen, size of the plating substrate, and the viability of the cells resident in the specimen. For samples which have been cryopreserved, we have found that a concentration of $5.0 \times 10^5$ mononuclear cells per ml of medium to about $2.0 \times 10^6$ mononuclear cells per ml of medium is preferred, with a concentration of about $1.0 \times 10^6$ mononuclear cells per ml of medium being most preferred. The cells mixed in the medium should be plated at a thickness which is achieved when a sample is mixed in 1 ml of culture media and plated in a 35 mm$^2$ culture dish. For samples which are fresh and plated within about 48 hours of collection, we have found that a concentration of $2.5 \times 10^5$ mononuclear cells per ml of medium to about $1.0 \times 10^6$ cells per ml of medium is preferred, with a concentration of about $5.0 \times 10^5$ cells per ml of medium being most preferred.

The components of the culture media used for the clonogenic assay will depend upon the type of suspected micro level tumor cells in the specimen, e.g. if the patient supplying the sample is diagnosed with breast cancer, possible metastatic breast tumor cells in the bone marrow would likely be suspected and should be assayed for.

The clonogenic assays described here are useful for the detection of viable metastatic or primary cancer cells at minute levels in hematopoietic samples, from, for example, adrenal, bladder, breast, central nervous system, colon, kidney, lung, ovary, pancreas, prostate, thyroid, upper airways (head and neck), uterus, bile ducts, skin, choriocarcinoma, esophagus, liver, small bowel, stomach, leukemias such as chronic lymphocytic leukemia, chronic myelocytic leukemia, acute lymphocytic leukemia, acute myelocytic leukemia, diffuse lymphomas, myeloma and the like.

The culture media will comprise as a base, a culture media which supports the growth of the normal hematopoietic cells in the sample. Though not intending to be bound by theory, we believe that the assay is particularly successful and useful because the hematopoietic cells are encouraged to grow and by such growth mimic the environment in which the tumor cells naturally reside. Media suitable for this purpose, includes for example, double strength RPMI-1640, lymphocyte-conditioned media (Advanced Biotechnologies Inc., Columbia, Md.) and high glucose Dulbecco's Modified Eagle's Medium (Sigma). The most preferred media is about 20% to about 40% (volume to volume) double strength Iscove's Modified Dulbecco's medium (Sigma Chemical Co., St. Louis, Mo.) supplemented with animal fetal serum, such as fetal bovine serum at a concentration of about 10% to about 30%, most preferably about 20% (volume to volume).

The semi-solid state of the clonogenic assay medium is critical for obtaining viable micro level tumor clone growth. A gelling agent which is non-toxic, retains water, allows for proper diffusion of growth factors and is not susceptible to drying and cracking is used to create the semi-solid state. Suitable gelling agents include agar, agarose, sea-prep agar, and methyl cellulose (all available from Sigma). A concentration of about 0.15 to about 0.6%, preferably about 0.3 to about 0.6% of agar is used, with concentrations for other gelling agents being adjusted accordingly. The gelling agent is combined with the other components of the culture medium to yield a single layer homogenous culture media.

Also important for the assay medium will be the addition of key growth factors at a concentration which will encourage the growth of the specific suspected micro level tumor cells and which will not prohibit the growth of the normal hematopoietic cells. Many growth factors are known and available, for example, the interleukins, colony stimulating factors (GM-CSF, G-CSF, M-CSF), insulin-like growth factors, transforming growth factors, epidermal growth factors, nerve growth factors, other cytokines and the like.

When metastatic breast tumor cells are targeted, a combination of human recombinant GM-CSF, human recombinant epidermal growth factor (EGF), and insulin growth factor-1 (IGF-1) is preferred (all available from Collaborative Research, Bedford, Mass.). The preferred concentration of GM-CSF is about 20 U to about 150 U/ml of medium, most preferably about 30 to about 90 U/ml of medium. ("U" refers to International Units.) The preferred concentration of EGF is about 1 to about 10 µg/ml of medium, preferably about 3 to about 7 µg/ml of medium. The preferred concentration of IGF-1 is about 0.05 to about 2.0 µg/ml of medium, most preferably about 1.0 µg/ml of medium.

When the targeted tumor cells are ovarian cancer, transforming growth factor—α (TGF-α) is a preferred growth factor. A preferred concentration for TGF-α is about 5 to about 15 µg/ml of medium, most preferably 10 µg/ml of medium.

When the targeted tumor cells are large cell lung cancer, the preferred growth factors are EGF and GM-CSF at the concentrations provided above. Platelet derived growth factor (PDGF) and IL-6 (both available from Collaborative Research) are also preferred growth factors. The preferred concentration of PDGF is about 5 to about 100 µg/ml of medium, most preferably about 20 to about 50 µg/ml of medium. The preferred concentration of IL-6 is about 5 to about 20 U/ml of medium, most preferably 10 U/ml of medium.

When the targeted tumor cells are prostate or colon, the preferred growth factors are EGF, GM-CSF, IGF-1 and PDGF at the concentrations specified above.

When the targeted tumor cells are small cell lung cells, melanoma cells or neuroblastoma cells, the preferred growth factors are 7S-NGF (Collaborative Research) at a preferred concentration of about 0.5 µg/ml to about 5 µg/ml, most preferably about 1 µg/ml and IGF-1 and GM-CSF at concentrations described above.

It may also be desirable to include antibiotics and/or anti-fungal agents in order to discourage the growth of contaminants.

The clonogenic assays described here are also particularly useful for detecting leukemia and non-Hodgkin's lymphoma. Growth factors which are important for targeting these tumor cells are GM-CSF and IL-6 at the concentrations described above. PDGF, IL-3 and IGF-1 are also particularly useful and may be included at the concentrations provided above.

Once prepared, the culture media is placed in appropriate tissue culture plates for plating of the cells. A thickness equivalent to that obtained when the cell sample and one ml of medium is plated in a 35 mm$^2$ culture dish is preferred. The plates are then incubated until the normal cells and targeted tumor cells grow into clonal colonies. It is desirable to allow the colonies to grow so that there are at least two tumor colonies that have 40 cells or more. Typically the plates are incubated in a humidified environment at about 35° C.–38° C., preferably about 37° C. in the presence of $CO_2$ (typically about 5–7.5% $CO_2$) for about 7–21 days, preferably about 8–14 days.

Once the clones are obtained, they may be removed and cultured on similar media for further testing. The colonies may be plucked out and individually stained. The tumor colonies present on the plate may be roughly characterized by their unique morphology through, for example, phase microscopy. They may also be identified and quantified by known immunocytological techniques or by any other appropriate methods available which can distinguish tumor cells from other cells. Any binding moiety such as a monoclonal antibody having specificity for the tumor cells to be targeted can be employed, for example, in detection of the tumors. An immunostaining technique using fluorescent monoclonal antibodies specific for the tumor cells is particularly useful and is preferred.

Any direct or indirect known means of labeling or detecting a binding moiety specific for the tumor cells can be employed here such as by the use of fluorescent products, enzymatic products, radiolabels, such as radioiodines ($^{131}I$ or $^{123}I$) or radiometals ($^{111}In$ or $^{99m}Tc$) and the like. The means of detection will then depend upon the nature of the label.

The semi-solid plating technique described above is advantageously adaptable to an immunostaining technique whereby one or more antibodies or other detectable binding moieties unique to tumor cell markers can be labeled and placed in contact with the tumor cell clones. Once the binding moieties are allowed to bind with the markers they are specific for, their presence can be detected and the presence of the tumor indicated. For example, two antibodies specific for different cell markers and labelled with different colored fluorescent tags to indicate that fact can be placed in contact with the plated cells. The presence or absence of tumor cells with one and/or the other marker can be observed by the presence of the particular tags when read under a fluorescent scope. Antibodies specific for the targeted tumor cells and antibodies specific for the hematopoietic cells which do not react with the tumor cells can also be employed and independently labeled to distinguish between the two cell groups. Binding moieties with relatively generic specificity for tumor cells, such as antibody P53 (Oncogene Science, Inc., Uniondale, N.Y.) which is reactive with a marker found on many different tumor cell types, can be used to aid in confirming the presence of tumor cells.

A preferred procedure for an immunostaining detection assay involves the following. The semi-solid culture medium is cooled and then released from the culture dish and placed on a slide. The slides are then incubated with detectable binding moieties, washed to remove excess binding moiety, and then read under a microscope.

We have found that the medium bearing the cells is most easily released from the culture dish by first cooling the dish under refrigeration (typically at 4° C.) until the media hardens. Then a small amount of distilled water is added to the dish to gently flood the hardened media away from the edges of the culture dish. The culture dish is then submerged in water until the water tension causes the hardened media to be released from the culture dish. Once released, the media is encouraged to float onto a slide and the water is aspirated. A filter that does not significantly absorb liquid such as a cellulose acetate filter can be placed over the wet slide to prevent uneven drying and cracking. The slide is then allowed to dry, preferably at 4° C. for at least 12 hours.

To stain the cells, the slides are preferably fixed, by, for example, treating with a non-aldehyde substance which will permit the binding moieties to contact and bind to the cells, such as absolute methanol, paraformaldehyde or paraformaldehyde in combination with methanol. Fixing typically takes place for about 15 minutes at room temperature or less, preferably at 4° C. After treatment they are then washed in a buffer solution, such as phosphate buffered saline (PBS) and treated with an enzyme or other substance to break up the media, such as agarase. The agarase treatment may be done using a minimal amount of agarase, such as 1–4, preferably about 2 µg/ml of buffer at about 37° C. for about 15–90 minutes, preferably about 30 minutes. The slides are then washed again in buffer solution. After this washing, the slides can be incubated with a solution of the binding moieties at conditions conducive to specific binding. The slides are then washed again with a buffer to remove unbound reagent. An additional detection agent can be added if appropriate for the binding moiety used. For example, if IgG monoclonal antibodies are used as the binding moiety, fluorescent labeled anti-IgG antibodies can be incubated with the slide to label the tumor cell-monoclonal antibody complex.

The tumor cells can also be detected and identified by flow cytometry or by other techniques which detect for specific nucleic acid such as oncogenes of interest, for example, in situ hybridization, polymerase chain reaction, electrophoresis and the like. Of further advantage here is the combination of the various detection techniques. For example, one could use the immunostaining technique to identify or characterize the tumor cells and then subject the stained cells to in situ hybridization to detect for particular genes of interest.

A plating efficiency for the assay can be determined by calculating the number of tumor cells plated by the number of tumor colonies that grew, with the quotient multiplied by 100. The plating efficiency indicates the percentage of viable tumor cells in the original sample.

Enrichment of Tumor Cells in the Sample for Use in the Assay

If desired, hematopoietic specimens can be pretreated to enrich the number of tumor cells in the cell sample to be assayed. In many cases this will enhance the likelihood that tumor cell clones will be obtained. To enrich the sample for tumor cells is to treat the patient sample such that the concentration of tumor cells is selectively increased over the hematopoietic cell concentration which existed in the sample as collected. Typically, one may either a) selectively isolate the tumor cells out from the hematopoietic cells (positive selection) and/or b) deplete the number of hematopoietic cells present in the marrow specimens, thereby enriching the number of tumor cells that remain (negative selection). If desired, the processes used to enrich the tumor cell population may be performed more than once or in any combination appropriate. When the enrichment step is employed, some hematopoietic cells will and should remain in the cell sample to be plated. Also, the enrichment techniques may be employed in combination with other culture techniques to selectively enhance the tumor cell concentration and growth.

Positive selection of tumor cells can be accomplished, for example, by biophysical separation techniques such as flow cytometry, lectin binding or by density gradient fractions that isolate cells into discrete centrifuged layers on the basis of cell size and density. Positive selection of tumor cells may also be accomplished by immunological means such as avidin-biotin systems, solid-phase binding or by separation of the tumor cells from the marrow cells by immunomagnetic removal and the like. Density gradient fractions, for example, have been applied to bone marrow to aid in the removal of tumor cells and may be used here to treat the cell samples prior to assaying the samples (Ellis et al., *J. Immunol. Meth.* 66: 9 (1984) Macfarlane, et al., *Am. J. Hematology* 22: 403–407 (1986); and Kies, et al., *Exp. Hematology* 16: 190–194 (1988) all of which are incorporated by reference herein).

Albumin-sucrose gradients such as Percoll are an example of a density gradient means to enrich tumor cell numbers from bone marrow specimens that have few tumor cells present. Percoll (Pharmacia, Upssala, Sweden) may be layered in progressive dilutions (30% to 100%, diluted with phosphate-buffered saline), with the bone marrow layered onto the top of the solution, and centrifuged at speeds ranging from about 50 g to 100 g for times ranging from about 10 to 30 minutes. The cells are then collected from the interface of each density layer. Immunocytochemical analysis, for example, can be used to determine which layer contains the greatest concentration of tumor cells.

A second exemplary method of enriching tumor cells in a specimen is to use an immunological method such as immunomagnetic separation of the cells. For example, the mononuclear cell fraction from the bone marrow specimen may be incubated with anti-tumor cell monoclonal antibodies (see, e.g., Table 1) (e.g. 200 μg antibody/ml medium) at 4° C. for 30–60 mins., then washed with RPMI medium supplemented with 10% fetal bovine serum (FBS) twice at 1200 RPM at 10 minutes each time. The specimens are then incubated with teflon-coated magnetic beads (Dynal, Olso, Norway) per the manufacturer's instructions at a bead:cell ratio of about 1:1 to 1:3 at 4° C. for about 30–60 minutes. The specimens are then washed in the RPMI/FBS medium twice at 1200 RPM at 10 minutes each time. Finally, the cell samples are secured in a magnetic device that draws the bound cells to the magnet and the cells are allowed to separate at room temperature for about 2–10 minutes. The unbound cells will be decanted from the specimen, and the bound cells will be released from the magnet. The beads can be removed from the cells by gentle centrifugation (600–800 RPM for 2–5 mins.) or by enzymatic treatment with chymopapain (Sigma Chemical Co., St. Louis, Mo.), for example, following release, the cells can be plated in the clonogenic assay described above.

An alternative or additional method of enriching tumor cells in a specimen is to decrease the number of hematopoietic cells in the bone marrow specimen (negative selection). This can be accomplished by, for example, immunological means such as complement mediated cytolysis, toxin, immunorosettes and immunomagnetic means in a procedure similar to that described above for positive tumor cell selection. Immunomagnetic depletion of marrow hematopoietic cells can be accomplished by incubating the mononuclear cell fraction of the marrow with an antibody specific for hematopoietic cells, such as an anti-CD45 monoclonal antibody, which binds to hematopoietic cells but not tumor cells. The procedure is the same as that described above except that the hematopoietic cells are isolated. In this case, the unbound cells are the tumor cells, which are removed from the tube in the magnetic device and then plated in the clonogenic assay. Other negative selection methods include biochemical means such as the use of selective cytotoxic drugs, anti-sense oligodeoxynucleotides, biophysical means such as phototherapy, adsorption columns, counter flow elutination and lectin agglutination and the like. Certain selection techniques such as the negative selection immunomagnetic means or density gradient means have the added advantage that they do not cause substantial manipulation of the tumor cells, which could otherwise impair tumor cell growth in culture.

Those of skill in the art will be able to adapt the tumor cell enrichment methods to the assay described herein. The addition of the enrichment step to the clonogenic assay will selectively enhance the number of tumor cells in marrow specimens that have low numbers of tumor cells present and thus allow one to use the clonogenic assay for a wider range of cancer patients.

Applications for the Assay

The clonogenic assay described here can be used to test the sensitivity or chemoresistance of particular tumor cells to known and established anti-neoplastic agents as well as promising new drugs. Such assays are particularly important where a patient has micrometastases. These cells quite often are not sensitive to the therapeutic agents applied to treat primary tumors. These cells tend also to have a higher degree of variability than primary tumors, making treatment tailored to the patient's particular cells advantageous. Since the clonogenic assay can be done over a period of time of 14 days or less, it is a practical means to quickly obtain information about which drugs should be used in treatment for a particular patient.

In carrying out such drug sensitivity measurements, the sensitivity of the tumor cells to exposure to one or more given dose levels of a given drug is measured by individually culturing aliquots of the same hematopoietic sample utilizing multiple clonogenic assays described here. One of the aliquots serves as a control and is quantitatively assayed for its viable colony-forming tumor cell content thereof in the absence of drug exposure. Each of the other of the aliquots is exposed to the drug at different dose levels which is then quantitatively assayed for a surviving drug-exposed colony-forming tumor cell content. The percent reduction in the assay count resulting from the drug exposure may then be determined for each of the drug levels tested.

Drug exposure of the cells may occur prior to plating of the aliquot in the culture media as a means for mimicking drug treatments where the patient is given one large dose of drug in a single administration. Alternatively, drugs to be tested may be added at varying dosages to the culture medium upon which the test aliquots are to be mixed. Preferably, drugs showing therapeutic potential will result in a 90% or greater reduction of tumor colony growth in the drug treated aliquots over the control aliquots.

Further, since the assay promotes the growth of both normal hematopoietic cells and tumor cells, a drug's toxicity to normal cells can be monitored in a similar manner as well. Thus, these assays uniquely permit the simultaneous testing of drug effects on both normal and tumor cells.

The assays of the present invention further provide a means to check the effectiveness of bone marrow purging techniques such as chemo-purging, antibody-directed purging, immuno-magnetic bead purging or photodynamic purging and the like or any other techniques used to otherwise manipulate hematopoietic products from hematopoietic sources. Procedures which positively select for bone marrow that includes desired cells, such as CD34 positive cells are example of procedures which could benefit by this assay. Samples of bone marrow prior to treatment such as purging and after a treatment can be assayed and compared.

The assays of the present invention further provide valuable and rapid information regarding the prognosis of a patient with micro levels of tumor cells. The presence of micrometastases, for example, is typically indicative of a worse prognosis than if no metastases are present. Since the clonogenic assay described here detects viable tumor cells, it is a more reliable indicator of the prognosis for a patient than detection systems that do not discriminate between viable and non-viable cells. Some researchers believe that the presence of dead or dormant cells results from the shedding of primary tumors. Such cells would not be able to set up secondary sites of disease and detection of their presence without knowing whether or not they would be viable would thus be misleading.

The assay can also be used as an indicator of the aggressiveness of the tumor existing at micro levels and thus prognosis. Where the plating efficiency of the tumors is high, $\geq 10\%$, prognosis would not be expected to be as good as in cases where the plating efficiency is low, $\leq 2\%$. It will also be useful to use the plating efficiency information in conjunction with tumor cell concentration. If a patient has a high plating efficiency and a high tumor cell count the prognosis would be expected to be considerably poorer than a patient who has a low plating efficiency and a low cell count. Prognosis would be adjusted accordingly for values in between those two extremes. Due to the short time period within which the assay is performed, this information can be used in conjunction with other prognostic factors available to the treating physician to enable her to better design treatment for the patient and to predict the course of the disease.

The following examples are provided for illustrative purposes and are not to be construed as limitations on the invention as claimed.

EXAMPLES

I. Clonogenic Assay for Micrometastases in Bone Marrow

A. Patient Population

Bone marrow (BM) or peripheral blood stem cell (PBSC) specimens were obtained from patients with histologically documented adenocarcinoma of the breast. The BM and PBSC specimens were received from private physicians and medical institutions. The BM aspirates were obtained from the posterior iliac crest, and the PBSC specimens were obtained from central venous catheters during pheresis sessions.

B. Collection of BM and PBSC Specimens

We have analyzed a total of 455 BM and PBSC specimens from breast cancer patients with the MCA assay. All specimens were processed for the MCA assay as follows:

1. Bone marrow aspirates containing at least $1 \times 10^7$ cells/ml were collected in sterile sodium heparin tubes and shipped at room temperature to us for immunocytochemical (ICC) and MCA analyses. The BM specimens averaged 3–5 ml per collection.

2. The PBSC specimens were shipped in aliquots containing at least $6 \times 10^6$ cells/ml from each pheresis session to us for ICC and MCA analyses.

3. In some cases BM and/or PBSC collections were cryopreserved in sterile culture media supplemented with fetal bovine serum (FBS; Sigma Chemical, St. Louis, Mo.) or autologous serum, with 10% dimethylsulfoxide (DMSO; Sigma) added as a cryoprotectant. The specimens were frozen under rate-controlled freezing conditions, stored in liquid nitrogen, and shipped on dry ice to us. BM and PBSC analyses are not adversely affected by the cryopreservation and thawing procedures. (Ross A. A., *Amer. J. Clin. Pathol.* 98:347 (1992); Chaiwun, et al., *Diagn. Oncol.* 2:267 (1992))

C. Processing of BM and PBSC Specimens for Immunocytochemical Analysis

Processing of BM and PBSC specimens proceeded as follows:

1. Mononuclear cells were isolated from BM and PBSC specimens by Ficoll-Hypaque (Pharmacia, Uppsala, Sweden) separation. Specimens were washed twice in Liebovitz L-15 medium (GIBCO/BRL, Grand Island, N.Y.) supplemented with 15% fetal bovine serum (Sigma) at 1500 RPM for 10 min.

2. Cryopreserved BM and PBSC specimens were thawed rapidly in a 37° C. water bath. To prevent specimen clotting caused by fibrin deposition that occurs during freezing procedures, cryopreserved BM and PBSC specimens were treated with 100 µl of Deoxyribonuclease I (Sigma) at 2000 Kunitz U/ml for 5 min at 37° C. The Deoxyribonuclease I degrades the DNA bonds of the fibrin and prevents clotting. The treated specimens were then washed twice with fetal bovine serum-free RPMI-1640 medium (Sigma) at 1500 RPM for 10 min. We found that it was advantageous to omit the fetal bovine serum in the cryopreserved specimens as traces of fibrin remaining in the specimens would react with the serum to cause further clotting.

3. To determine the number of tumor cells in the specimens, $2.5-5.0 \times 10^6$ cells were then used for ICC analysis and the remaining cells were used for MCA analysis.

4. For ICC analysis, cells were spun onto glass slides with a Shandon cytospin (Shandon, Pittsburgh, Pa.) and allowed to dry overnight at 4° C. Cytopreparations were fixed overnight in a 1:1 4% paraformaldehyde/absolute methanol fixative (pH 7.4) at 4° C. for 30 min. Slides were then washed in Dulbecco's modified phosphate-buffered saline (PBS) solution (Sigma) at room temperature twice for 5 min each. Endogenous peroxidase activity was then blocked using a 50 mM solution of phenylhydrazine in PBS for 20 min at 37° C. Following additional PBS washes, the slides were incubated in 10% normal goat serum (Zymed, So. San Francisco, Calif.) at 37° C. for 30 min to block nonspecific protein binding. The slides were then incubated with a cocktail mixture of murine monoclonal antibodies that react with epithelial cell-specific and breast carcinoma-associated antigens (Table 1). Following additional PBS washes, the slides were immunostained with amino-ethylcarbazol as the chromogen with the Zymed AEC kit according to manufacturer's instructions. With this ICC procedure, the tumor cells stain bright red, while the hematopoietic cells stain blue.

TABLE 1

Monoclonal antibodies used for immunocytochemical analysis

| Monoclonal Antibody (source) | Reactive Antigen | Reactive Cell Type |
|---|---|---|
| MAS-385 (Accurate Chemical; Westbury, NY) | human mammary carcinoma-associated antigen | breast epithelium |
| SB-3 (CalTag; San Francisco, CA) | 8,18,19 kD cytokeratin | glandular epithelium |
| TFS-2 (Biodesign; Kennebunkport, ME) | cellular adhesion molecule | breast epithelium, small cell lung cancer |
| SB-6 (Accurate Chemical)NCAM | | breast epithelium, small cell lung cancer |
| 520C9 (Baxter Healthcare, Santa Ana, CA) | breast glycoprotein | breast epithelium |
| 260F9 (Baxter) | breast glycoprotein | breast epithelium |
| 317G5 (Baxter) | breast glycoprotein | breast epithelium |

D. Clonogenic Assay

Processing of BM and PBSC specimens for the MCA assay were performed as follows:

1. Mononuclear cells were isolated from the BM and PBSC specimens as described above. For fresh BM or PBSC specimens, $5.0 \times 10^5$ mononuclear cells were plated in 1 ml of MCA medium in each 35 mm$^2$ culture dish. For cryopreserved BM and PBSC specimens, $1.0 \times 10^6$ mononuclear cells were plated in 1 ml of MCA medium. The additional cells in cryopreserved specimens were plated to compensate for reduced mononuclear cell viabilities. All specimens were plated in triplicate in 35 mm$^2$ grid-bottom petri dishes (Nunc, Inc., Naperville, Ill.).

2. The MCA culture medium contained the following volume/volume elements:
   a. 30% Iscove's Modified Dulbecco's Medium (IMDM; Sigma), 20% fetal bovine serum (Sigma), and 50% of a 0.6% agar solution (Sigma). 5 U penicillin/streptomycin/gentamicin (Sigma) is added to 1 ml of medium to prevent bacterial and fungal growth. The solution was prepared at 37° C. to allow the elements to mix. Appropriate cell volumes were added to the mixture to bring the final cell volume to the appropriate concentrations for fresh and cryopreserved specimens.
   b. We tried various combinations of growth factors to optimize tumor colony growth. While some growth factors, such as transforming growth factor-alpha, were inhibitory to tumor colony growth, we settled on the following human recombinant growth factors as comprising the best tumor cell growth-enhancing combination. Thus, the following combination of growth factors was added to the culture dishes prior to plating the cells in the MCA culture medium:
      i. GM-CSF (Collaborative Research, Bedford, Mass.) was added at a final concentration of 50 U/ml of medium.
      ii. Epidermal growth factor EGF; Collaborative Research) was added at a final concentration of 5 µg/ml of medium.
      iii. IGF-1 (Collaborative Research) was added at a final concentration of 0.1 µg/ml of medium.
      iv. In order to assess the effects of the recombinant growth factors on the tumor cells in the MCA assay, additional "negative control" plates consisted of cells plated in the MCA medium without the added growth factors.
   c. All plates were incubated in a humidified chamber at 37° C. with 7.5% $CO_2$ for 14 days. Tumor colonies were preliminarily estimated under phase microscopy by their unique morphology. The preliminary estimated tumor colonies were counted for each culture dish, with a minimum of two colonies consisting of >40 cells being required to be considered positive for colony growth.

E. Tumor Colony Identification

Following tumor colony estimation by phase microscopy, verification of colonies as tumor-derived was performed as follows:

1. MCA culture plates containing the semi-solid agar medium (SAM) were placed in a 4° C. refrigerator for 1 hr to allow the SAM to harden. Next, 3 ml of distilled water was added to the culture dish, and a glass pipette was used to gently flood the SAM away from the edges of the culture dish. The culture dish was then placed in a large flat-bottomed dish containing 400 ml of distilled water. The culture dish was gently submerged in the water until the water tension caused the SAM to be released from the culture dish and to gently float on the water surface. A large 2"×3" microscope slide was placed under the floating SAM, and the water was aspirated, which allowed the SAM to float gently onto the microscope slide. A cellulose acetate filter was placed over the wet SAM to prevent uneven drying and cracking, and the slide was allowed to dry overnight at 4° C.

2. Tumor colony verification and quantification was performed using immunostaining with the same monoclonal antibodies that were used to identify tumor cells in the ICC assay (Table 1). However, because high levels of neutrophilic peroxidase are present in hematopoietic colonies in the MCA, it was advantageous to perform the immunostaining verification with immunofluorescent staining rather than immunoperoxidase staining. The staining procedure was performed as follows:
   a. The slides were fixed with absolute methanol for 15 min at 4° C.
   b. The slides were washed thoroughly in PBS (phosphate buffered saline).
   c. The slides were treated with a 1 ml. solution of agarase (New England BioLabs (Beverly, Mass.) at 2 µg/ml at 37° C. for 30 min.
   d. The slides were washed thoroughly with PBS.
   e. The slides were incubated with the antibodies at 5 µg/ml at 37° C. for 1 hr.
   f. The slides were washed thoroughly in PBS.
   g. The slides were incubated with FITC (fluorescein isothiocyanate)-conjugated IgG (Sigma) at a 1:40 dilution at room temperature for 2 hours.
   h. The slides were washed thoroughly with PBS.
   i. In some cases the slides were also incubated with CD11 and CD33 antibodies which are anti-pan myeloid cell antibodies to further indicate the differences in the cell types present and then washed with PBS. When the CD11 and CD33 antibodies were used, they were stained with rhodamine-conjugated antibodies and washed with PBS resulting in slides with dual color indicators showing the different cell types present. Likewise, in some cases the slides were also incubated with P53 antibody (Advanced Biotechnologies, Inc.), washed with PBS and stained.

j. The slides were coverslipped with Crystalmount (Sigma) and read under a fluorescent microscope.

F. Cell Lines and Seeding Experiments.

The human breast cancer continuous cell line CAMA-1 was seeded into five tumor-free bone BM or PBSC specimens at tumor cell: hematopoietic cell ratios ranging from 1:1000 to 1:100,000. These tumor cell-seeded specimens were plated into the MCA assay as above. These experiments were done to determine the effects of the various growth factor combinations on the plating efficiency (calculated as the number of tumor colonies that grow divided by number of tumor cell seeded cells, with the quotient multiplied by 100) of the tumor cells. The plating efficiency is a measurement of how well the tumor cells grow in a growth factor-rich environment, and, thus, may be an indicator of their potential for metastatic growth in the bone marrow and other organs.

The observed plating efficiency for seeded CAMA-1 breast cancer cells averaged 21% for growth factor-supplemented plates and 8.6% for non-supplemented control plates. These experiments demonstrated that the particular combination of growth factors we used was able to significantly enhance the ability of breast cancer cells to grow in the MCA system in spite of concurrent growth of normal cells.

In additional experiments, BM specimens from patients without breast cancer, or from patients with hematologic malignancies showed no growth of colonies that were identified as breast cancer-derived by morphology or by immunofluorescent staining with the cocktail of monoclonal antibodies.

G. MCA for tumor micrometastases in bone marrow specimens of breast cancer patients.

We have analyzed 371 BM specimens from breast cancer patients in the MCA assay. Thirty of the 371 MCA experiments (8%) were lost to bacterial contamination, although the bacterial contamination was greatly reduced in the last 100 samples.

One hundred seventy-three of the 371 BM (46.6%) specimens grew identifiable tumor colonies (Table 2). Of these 173 MCA-positive specimens, 163 (94.2%) were positive for tumor cells by ICC analysis. Ten of the specimens (5.8%) that were negative for the presence of tumor cells by ICC analysis grew tumor colonies in the MCA assay. Of nine BM specimens that were indeterminate for the presence of tumor by ICC analysis (equivocal immunostaining results), three (33.3%) grew tumor colonies in the MCA assay. Thus, the MCA assay was a confirmatory test for incorrect or ambiguous immunostaining results in several cases. Chi Square analysis revealed that tumor colony growth in the MCA assay correlated with ICC analysis for the presence of tumor cells at the highly significant 0.0001 confidence level.

TABLE 2

Bone marrow specimens analyzed by the MCA assay

| | | MCA Results + | MCA Results − |
|---|---|---|---|
| ICC Analysis | + | 163 | 12 |
| | − | 10 | 186 |
| Total: | | 173 | 198 |

One hundred ninety-eight of the 371 BM specimens (53.4%) did not grow tumor colonies in the MCA assay (Table 2). Of the 198 MCA-negative specimens, 12 specimens (6.0%) were positive for tumor cells by ICC analysis. It may be that some tumor cells in the BM represent a group of tumor cells that are: a) non-viable cells that have been trapped in the marrow matrix and have no potential for clonogenic growth; b) are viable cells, but are in a low synthesis state, and therefore are cells with a low metastatic potential; or c) the plating efficiency was too low to result in clonogenic growth.

H. MCA for tumor micrometastases from PBSC specimens from breast cancer patients Eighty-four MCA's from PBSC collections from breast cancer patients were performed (Table 3). Six of the 84 PBSC specimens (7.1%) showed tumor colony growth in the MCA assay. Of the six MCA-positive specimens, four were positive for tumor cells by ICC analysis and two were indeterminate by ICC analysis. Two PBSC specimens that were ICC-positive for tumor cells did not grow tumor colonies in the MCA assay. Of the 78 MCA-negative PBSC specimens, none was positive for tumor cells by ICC analysis.

TABLE 3

Peripheral blood stem cell specimens analyzed by the MCA assay

| | | MCA Results + | MCA Results − |
|---|---|---|---|
| ICC Analysis | + | 6* | 2 |
| | − | 0 | 78 |
| Total: | | 6 | 80 |

*Includes 2 specimens that were indeterminate by ICC analysis

I. Verification and Quantification of colonies as tumor-derived

Verification of colonies as tumor-derived consisted of the combination of colony morphology by phase microscopic analysis and the immunofluorescent staining of the colonies with the same panel of breast cancer-associated monoclonal antibodies used for the detection of tumor cells by ICC. The colonies showed a pronounced filamentous cytoplasmic staining with anti-cytokeratin antibody SB-3 and membrane staining with the membrane-associated breast antibodies.

J. Plating efficiencies of fresh versus cryopreserved specimens.

Percentage plating efficiency for tumor cells was calculated by dividing the number of tumor cells plated by the number of tumor colonies that grew, with the quotient multiplied by 100:

$$\frac{\text{\# tumor colonies}}{\text{\# tumor cells plated}} \times 100$$

The plating efficiency percentage for the fresh BM and PBSC specimens ranged from 4% to 30% with a median of 5%. For cryopreserved BM and PBSC specimens the range of plating efficiencies was 0.3% to 15% with a median of 1%. These results suggest that viability and plating efficiency was better in fresh specimens than in cryopreserved specimens.

K. Pretreatment of specimens to enrich for tumor cells.

Four experiments were performed with breast cancer cell lines seeded into normal bone marrow specimens at varying concentrations to test the tumor enriching capabilities of hematopoietic cell depletion by immunomagnetic separation.

Breast cancer cell lines CAMA-1 and MCF-7 were seeded into normal bone marrow specimens at concentrations ranging from 0.1% to 1.0% total volume of tumor cells. The cells were incubated with an anti-CD45 monoclonal antibody which binds to hematopoietic cells at a concentration of 100 µg/ml of cell volume and incubated on ice for 1 hr. The cells were then washed twice at 1200 RPM at 10 min. each time with RPMI 1640 medium supplemented with 2% fetal bovine serum (FBS). The cells were then incubated with IgG-coated Dynal immunomagnetic beads at a bead:cell ratio of about 1:1 and incubated on ice for 1 hr. The cell suspension was then placed in a magnetic column device that pulls the bound cell:bead complexes to the magnet. The unbound cells (which includes the tumor cells) were aspirated from the tube and washed twice as described above in RPMI 1640/FBS media. The cells were then plated in the clonogenic assay as described above at a concentration of $5.0 \times 10^5$ cells per dish. Control specimens at each tumor cell concentration were similarly plated which were not subjected to the anti-CD45 antibody separation protocol. After 14 days in culture, the tumor colonies in the control and test plates were counted under phase microscopy and stained by immunofluorescence with the panel of anti-breast cancer antibodies. The results of the experiments were as follows:

| Breast Cancer Cell Line (concentration) | Average # Tumor Colonies/Dish | |
|---|---|---|
| | Pre-separation | Post-separation |
| CAMA-1 (0.1%) | 0 | 305 |
| CAMA-1 (0.5%) | 15 | 625 |
| CAMA-1 (1.0%) | 40 | 7500 |
| MCF-7 (0.5%) | 2 | 175 |

As can be seen by the results, the number of tumor colonies/plate was increased dramatically by the pretreatment process.

II. MCA ASSAY FOR PROGNOSIS

Since the discovery that the bone marrow appears to be a reservoir for low numbers of tumor cells in patients with no clinically apparent metastatic disease, the concern has been raised that these cells are merely dead cells that have been shed from the primary tumor and, therefore, cannot set up secondary sites of disease. Additionally, some researchers have reported that the tumor micrometastases disappear from the BM following tumor-removing surgery (Mansi, et al., *J. Clin. Oncol.* 7: 445 (1989). There is evidence that breast cancer patients with BM micrometastases have a worse prognosis than those who are micrometastases-free. It is not known if all cells in the BM micrometastases have the capacity to establish secondary sites of disease, or if the patient's prognosis is related to the exact numbers of micrometastatic tumor cells.

The assay described here has the ability to answer these crucial questions. As stated above, there was a wide range of plating efficiencies observed in the BM and PBSC specimens. Given that the percentage plating efficiency itself is independent of the number of cells plated, plating efficiency reflects the aggressive growth kinetics of each patient's individual tumor. A high plating efficiency indicates a more pervasive condition and represents one prognostic indicator that can indicate a relatively poor prognosis. A low plating efficiency indicates a less aggressive condition and represents one prognostic indicator that can indicate a relatively more promising prognosis. The assay has the potential to be of prognostic significance in determining the growth potential of a patient's tumor at the earliest stages of metastasis. Our data further suggest that the presence and growth of micrometastases in BM harvests of breast cancer patients who receive autologous BM transplants following high-dose chemotherapy is associated with poor post-transplant outcome (Ross, et al., *Breast Cancer Res. Treat.* 23: 166 (1992)).

The information gained on the growth kinetics of an individual patient's micrometastatic disease will provide valuable clinical information for the treating oncologist. In early stage patients, such prognostic information is solely based upon analysis of the primary tumor at time of surgery. The patient's prognosis is then extrapolated from data obtained from the primary tumor. Our assay, on the other hand, has the ability to isolate metastatic cells at the earliest stage of pre-clinical detection, and measures the growth potential of the actual metastatic cells. The clonogenic assay data will allow the oncologist to "custom design" treatment for each patient based on the unique growth characteristics of her tumor cells.

Additionally, the assay provides unique information as to the patient's response to chemotherapy. We have tested nine breast cancer patients with the MCA assay as they are being treated with chemotherapy. A reduction of the overall tumor burden in the BM and the disappearance of tumor colonies in the MCA assay was observed in three of the nine patients between cycle two and cycle five of chemotherapy. Thus, a patient's favorable response to chemotherapy can be documented.

III. IN VITRO DRUG ASSAY FOR MICROMETASTASES

Drug sensitivity testing using the clonogenic assay may be conducted as follows:

A. Mononuclear cell fractions are isolated from BM specimens as outlined under "Processing of BM and PBSC Specimens for Immunocytochemical Analysis" in Example 1. Prior to plating in the culture dishes, the cells are treated in one of two ways:

1. Cells are incubated with varying concentrations of the drugs to be tested in vitro at 37° C. for 1 hr. The drug concentrations are extrapolated to in vitro dosages according to treatment protocols[13]. Following incubation, cells are washed twice in fresh L-15/FBS at 1200 RPM for 10 min each. Cells are then plated according to methods outlined under "Micrometastasis Clonogenic Assay" in Example 1. This protocol is designed to mimic "bolus" drug treatment, where the patient is given one large dose of drug in a single administration.

2. Drugs are added directly to the culture plates immediately prior to cell plating. The drugs remain in the culture medium for the duration of the 14 day culture.

3. Control plates are set up for each patient, which consist of the patients BM specimen without the added drugs.

B. After a 14 day culture time has been completed, the drug-treated plates are compared to the control plates for the tumor colony quantitation. Successful drug treatment is defined as a 90% reduction of tumor colony growth in the drug treated plates over the control, non-treated plates.

Since a majority of breast cancer patients at relapse have marrow metastases, the assay can be used for in vitro drug sensitivity testing to test new compounds. This would allow new compounds to be tested against metastatic human cancer cells in their naturally occurring marrow environment. Not only would this allow researchers to study the tumor-suppressing effects of the drugs, it would allow toxicity parameters to be examined by monitoring the hematopoietic-lethal dosages of the drugs.

Current animal models and in vitro drug sensitivity systems on primary human tumor explants do not allow for the dual monitoring of drug effects on malignant and normal cells in the same assay (Weisenthal L. M., *Drug and Hormonal Resistance in Breast Cancer*, in press.). The assay described here would allow for this unique method to screen new tumoricidal compounds. Testing of new compounds could be performed as outlined above.

IV. EXAMPLE OF EFFICACY OF PURGING ASSAY

The assay provides additional confirmation of tumor cell purging methods in bone marrow harvested for autologous transplantation. Chemotherapeutic agents, such as 4-hydroperoxycyclophosphamide (4-HC), which is the active in vitro metabolite of the anticancer drug CYTOXAN, are used increasingly for purging marrow of tumor cells. However, little is known regarding the efficacy of such purging treatment. Our assay is ideal to monitor efficacy of purging and drug-induced hematopoietic cytotoxicity by quantitating pre- and post-purge tumor and hematopoietic colonies.

We have used the assay in this manner to test the residual growth of tumor colonies in BM specimens that had been treated in vitro with the drug. The assay was able to prove that residual tumor cells in the patients' BM were rendered incapable of colony growth following in vitro treatment. Thus, even though the ICC analysis documented that tumor cells were detectable following in vitro treatment with 4-HC, the assay showed that they were non-viable cells and were rendered incapable of further growth.

Because chemotherapeutic purging of marrow is toxic to hematopoietic cells, non-drug methods of tumor cell purging have been explored. These methods include, for example, those based upon removing tumor cells via magnetic beads that are conjugated to tumor cells by monoclonal antibodies and are passed over a strong magnetic field. The BM specimen is first incubated with monoclonal antibodies that are specific for tumor cells, then IgG-coated magnetic beads are added to the specimen. The IgG binds to the antibody-coated tumor cells, and the specimen is placed over the magnetic field apparatus.

Five marrow specimens that have had breast cancer cells seeded in for efficacy of magnetic removal have been analyzed. Our ICC analysis showed that a few tumor cells do remain in the BM following magnetic treatment (average log reduction of tumor cells=5 logs). However, the assay was able to show that even though a few tumor cells remained, the immunomagnetic purging process somehow rendered them incapable of further clonogenic growth. Thus, the assay provided crucial data that could not have been obtained by other previously known methods.

What is claimed is:

1. A clonogenic tumor cell assay for detecting viable micro levels of metastatic tumor cells resident in a patient hematopoietic sample comprising:

(a) obtaining a hematopoietic cell sample containing micro levels of metastatic tumor cells;

(b) plating tumor cells and hematopoietic cells from the sample on homogeneous culture media which supports growth of normal hematopoietic cells comprising (i) a gelling agent; and (ii) at least one growth factor which stimulates the growth of the tumor cells wherein the growth factor is selected from the group consisting of GM-CSF at a concentration of about 20 to about 150 U/ml of media, EGF at a concentration of about 1 to about 10 µg/ml of media, IGF-1 at a concentration of about 0.05 to about 2.0 µg/ml of media, TGF-α at a concentration of about 5 to about 15 µg/ml of medium, PDGF at a concentration of about 5 to about 100 µg/ml of media, Nerve Growth Factor at a concentration of about 0.5 to about 5 µg/ml of media, and IL-6 at a concentration of about 5 to about 20 U/ml of media; wherein the cell sample is plated at a concentration to yield both individual viable normal cell and tumor cell clones;

(c) incubating the cell sample plate to obtain growth of the clones; then, (d) detecting the presence of tumor cell clones.

2. The assay of claim 1, wherein the growth factor is GM-CSF present in the culture media at a concentration of about 20 U to about 150 U/ml of media.

3. The assay of claim 2, wherein the culture media further contains EGF at about 1 to about 10 µg/ml of media.

4. The assay of claim 1, wherein the growth factor is TGF-α present in the culture media at a concentration of about 5 to about 15 µg/ml of media.

5. The assay of claim 1, wherein the culture media contains IGF-1 at a concentration of about 0.05 to about 2.0 µg/ml of media.

6. The assay of claim 1, wherein the culture media further contains animal fetal serum at a volume to volume concentration of about 10 to about 30%.

7. The assay of claim 1, wherein the micro tumor cells are those selected from the group consisting of breast tumor cells, ovarian tumor cells, melanoma cells, neuroblastoma cells, colon tumor cells, prostate tumor cells, large cell lung tumor cells and small cell lung tumor cells.

8. The assay of claim 1, wherein the tumor cells are detected by immunocytochemical means.

9. The assay of claim 8, wherein the tumor cells are detected by cooling the cell sample clones on the culture media, placing the clones and the culture media on a slide, incubating the clones with a binding moiety specific for a tumor cell marker to create a binding moiety-tumor cell complex and then detecting the presence of the complex.

10. The assay of claim 9, wherein the clones are incubated with a second binding moiety specific for a second cell marker to create a second binding moiety-cell complex and detecting the presence of the second complex.

11. The assay of claim 1, wherein the gelling agent is agar present in the culture medium at a concentration of about 0.15 to about 0.6%.

12. The assay of claim 1, comprising the additional step of enriching the tumor cell concentration in the hematopoietic sample by depleting the number of hematopoietic cells after step (a) and before step (b).

13. An in vitro method for measuring drug sensitivity of a micro tumor cell as an indication of the antineoplastic activity of the drug against said tumor cell, said method comprising individually subjecting a test aliquot and a control aliquot of a patient hematopoietic specimen containing suspected micro tumor cells and normal hematopoietic cells to an assay procedure for quantitatively determining the viable colony-forming tumor cell contents thereof, said test aliquot differing from said control aliquot in having been subjected to exposure with the drug to be tested, whereby the drug sensitivity at the drug exposure dose level tested may be determined as the percent reduction in the assay count resulting from the drug exposure, said assay procedure employing the following:

(a) plating the test and the control aliqouts on homogeneous culture media which supports growth of normal hematopoietic cells comprising (I) a gelling agent; (ii) at least one growth factor which stimulates the growth of the tumor cells wherein the growth factor is selected from the group consisting of GM-CSF at a concentration of about 20 to about 150 U/ml of media, EGF at a concentration of about 1 to about 10 µg/ml of media, IGF-1 at a concentration of about 0.05 to about 2.0 µg/ml of media, TGF-α at a concentration of about 5 to about 15 µg/ml of media, PDGF at a concentration of about 5 to about 100 µg/ml of media, Nerve Growth Factor at a concentration of about 0.5 to about 5 µg/ml of media, and IL-6 at a concentration of about 5 to about 20 U/ml of media; wherein the aliquots are plated separately at a concentration to yield individual viable normal hematopoietic and tumor cell clones; and (b) incubating the cells to obtain growth of the clones; then, (c) determining the number of micro tumor cell clones in the test and control aliquot plates; wherein (d) a reduction of tumor colony growth indicates antineoplastic activity of the drug.

14. The method of claim 13, wherein the test aliquot is subjected to the drug prior to mixing the test aliquot with the culture media.

15. The method of claim 13 wherein the test aliquot is subjected to the drug when plated in the culture media which contains the drug.

16. A method for determining the effectiveness of a bone marrow treatment technique comprising, testing a specimen of bone marrow cells prior to a treatment (pre-treatment cells) and a specimen of bone marrow cells after a treatment (post-treatment cells) for tumor cells of interest by:

(a) plating each specimen on homogeneous culture media which supports growth of bone marrow cells comprising (I) a gelling agent; (ii) at least one growth factor which stimulates the growth of cells of interest wherein the growth factor is selected from the group consisting of GM-CSF at a concentration of about 20 to about 150 U/ml of media, EGF at a concentration of about 1 to about 10 µg/ml of media, IGF-1 at a concentration of about 0.05 to about 2.0 µg/ml of media, TGF-α at a concentration of about 5 to about 15 µg/ml of media, PDGF at a concentration of about 5 to about 100 µg/ml of media, Nerve Growth Factor at a concentration of about 0.5 to about 5 µg/ml of media, and IL-6 at a concentration of about 5 to about 20 U/ml of media; wherein the cells are plated at a concentration to yield individual viable clones of bone marrow cells; and (b) incubating the cells to obtain growth of the clones; then, (c) detecting the presence and number of individual clones of cells of interest, resulting from the culturing of each specimen; wherein, (d) no clonogenic growth of post-treatment tumor cells indicates effectiveness of the bone marrow treatment technique.

17. A clonogenic assay for determining a prognostic factor useful in the prognosis of a patient suspected of having metastatic tumor cells comprising:

(a) plating a patient bone marrow specimen containing suspected micrometastatic tumor cells and bone marrow cells on homogenous culture media which supports growth of bone marrow cells comprising (i) a gelling agent; (ii) at least one growth factor which stimulates the growth of the tumor cells wherein the growth factor is selected from the group consisting of GM-CSF at a concentration of about 20 to about 150 U/ml of media, EGF at a concentration of about 1 to about 10 µg/ml of media, IGF-1 at a concentration of about 0.05 to about 2.0 µg/ml of media, TGF-α at a concentration of about 5 to about 15 µg/ml of medium, PDGF at a concentration of about 5 to about 100 µg/ml of media, Nerve Growth Factor at a concentration of about 0.5 to about 5 µg/ml of media, and IL-6 at a concentration of about 5 to about 20 U/ml of media; wherein the cells are plated at a concentration to yield individual viable bone marrow and tumor cell clones; and (b) incubating the cells to obtain growth of the clones; then, (c) determining the number of individual clones of viable micrometastatic tumor cells as an indication of the prognosis of the patient, wherein the prognosis indicated is increasingly poorer as the number of colonies increases.

* * * * *